US009948642B2

(12) United States Patent
Wang et al.

(10) Patent No.: US 9,948,642 B2
(45) Date of Patent: *Apr. 17, 2018

(54) MULTI-MODAL BIOMETRIC IDENTIFICATION

(71) Applicants: Anhui Huami Information Technology Co.,Ltd., Hefei, Anhui (CN); Huami Inc., Mountain View, CA (US)

(72) Inventors: Fei Wang, Mountain View, CA (US); Ting Chen, Mountain View, CA (US); Yajun Zhao, Anhui (CN)

(73) Assignees: Anhui Huami Information Technology Co., Ltd., Hefei, Anhui (CN); Huami Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/691,968

(22) Filed: Aug. 31, 2017

(65) Prior Publication Data
US 2017/0366543 A1    Dec. 21, 2017

Related U.S. Application Data

(63) Continuation of application No. 14/869,088, filed on Sep. 29, 2015, now Pat. No. 9,787,676.

(51) Int. Cl.
*A61B 5/02* (2006.01)
*H04L 29/06* (2006.01)
(Continued)

(52) U.S. Cl.
CPC .......... *H04L 63/0861* (2013.01); *A61B 5/021* (2013.01); *A61B 5/04012* (2013.01);
(Continued)

(58) Field of Classification Search
CPC ..... A61B 5/6803; A61B 5/742; A61B 5/0245; A61B 5/002; A61B 5/021; A61B 5/04012;
(Continued)

(56) References Cited

U.S. PATENT DOCUMENTS 4,809,705 A    3/1989  Ascher
6,970,737 B1  11/2005  Brodnick et al.
(Continued)

FOREIGN PATENT DOCUMENTS

CN    103284702 A    9/2013
CN    103598877 A    2/2014
(Continued)

OTHER PUBLICATIONS

Agrafioti, F.; Hatzinakos, D.:ECG Based Recognition Using Second Order Statistics. Communication Networks and Services Research Conference, vol., No., pp. 82,87, 5-8 (2008).
(Continued)

*Primary Examiner* — Ali Neyzari
(74) *Attorney, Agent, or Firm* — Young Basile Hanlon & MacFarlane, P.C.

(57) ABSTRACT

At least two biometric measurement signals are generated by contact with a single individual. At least one feature is extracted from each signal of the at least two biometric measurement signals, the extracted features are combined to generate a combined biometric signal. The combined biometric signal is compared with a defined biometric signal associated with a known individual, responsive to the combined biometric signal matching the defined biometric signal, a signal is transmitted indicating that the single individual is the known individual. The biometric measurement signals can be collected by a biometric identification device worn or carried by the single individual. The processing may be done by the biometric identification device or a remote server.

20 Claims, 9 Drawing Sheets

(51) Int. Cl.
*A61B 5/04* (2006.01)
*A61B 5/021* (2006.01)
*A61B 5/00* (2006.01)
*A61B 5/0245* (2006.01)

(52) U.S. Cl.
CPC ............ *A61B 5/6803* (2013.01); *A61B 5/742* (2013.01); *H04L 63/10* (2013.01); *A61B 5/0245* (2013.01)

(58) Field of Classification Search
CPC ... A61B 5/14865; A61B 5/6893; H04L 63/10; H04L 63/0861
USPC ................................................ 340/5.52, 5.53
See application file for complete search history.

(56) References Cited

U.S. PATENT DOCUMENTS

| | | |
|---|---|---|
| 7,171,269 B1 | 1/2007 | Addison et al. |
| 7,630,521 B2 | 12/2009 | Kim et al. |
| 8,762,733 B2 | 6/2014 | Derchak et al. |
| 9,603,556 B2 | 3/2017 | Silva et al. |
| 9,633,168 B2 | 4/2017 | Lindsay |
| 9,787,676 B2 * | 10/2017 | Wang ................. H04L 63/0861 |
| 2003/0135097 A1 | 7/2003 | Wiederhold et al. |
| 2006/0106571 A1 | 5/2006 | Kim et al. |
| 2006/0161065 A1 | 7/2006 | Elion |
| 2007/0253624 A1 | 11/2007 | Becker |
| 2010/0090798 A1 | 4/2010 | Garcia Molina et al. |
| 2011/0254662 A1 | 10/2011 | Lindsay |
| 2014/0120876 A1 | 5/2014 | Shen |
| 2014/0188770 A1 | 7/2014 | Agrafioti et al. |
| 2014/0361871 A1 | 12/2014 | Silva et al. |
| 2015/0135310 A1 | 5/2015 | Lee |
| 2015/0199010 A1 | 7/2015 | Coleman et al. |
| 2015/0220716 A1 | 8/2015 | Aronowitz et al. |
| 2016/0270668 A1 | 9/2016 | Gil |
| 2016/0367138 A1 | 12/2016 | Kim et al. |
| 2016/0378965 A1 | 12/2016 | Choe et al. |

FOREIGN PATENT DOCUMENTS

| | | |
|---|---|---|
| CN | 104523266 A | 4/2015 |
| EP | 2526859 A1 | 11/2012 |
| KR | 20150029105 A | 3/2015 |
| WO | 2004030756 A1 | 4/2004 |
| WO | 2014022906 A1 | 2/2014 |
| WO | 2015047015 A1 | 4/2015 |
| WO | 2015051253 A2 | 4/2015 |

OTHER PUBLICATIONS

Biel L. et al. ECG analysis: A new approach in human identification. IEEE Trans. Instrum. Meas. 2001;50:808-812.
Chiu C.C., et. al. A Novel Personal Identity Verification Approach Using a Discrete Wavelet Transform of the ECG Signal. MUE 2008; Busan, Korea. Apr. 24-26, 2008; pp. 201-206.
Deep Learning and Biometrics http://icb2015.org/media/DL-Bio-final.pdf.
DeepID2 http://blog.csdn.net/stdcoutzyx/article/details/41497545.
Jin LinPeng, Dong Jun. Deep learning research on clinical electro-cardiogram analysis. , 2015, 45(3): 398-416.
Kaguara, Antony, Kee Myoung Nam, and Siddarth Reddy. "A deep neural network classifier for diagnosing sleep apnea from ECG data on smartphones and small embedded systems."
Kavasaoglu, A. Resit, Kemal Polat b, n, M. Recep Bozkurt a, A novel feature ranking algorithm for biometric recognition with PPG signals, Computers in Biology and Medicine 49, 2014.
Lugovaya T.S. Biometric human identification based on electrocardiogram. [Master's thesis] Electrotechnical University "LETI", Saint-Petersburg, Russian Federation; Jun. 2005.
Shen T. W. Ph.D. Thesis. University of Wisconsin; Madison, WI, USA: 2005. Biometric Identity Verification Based on Electrocardiogram (ECG).
Singh, Y.N.; Gupta, P.: ECG to Individual Identification. In: Proc. of the 2nd IEEE BTAS Conf., pp. 1-8 (2008).
Stober, Sebastian, Daniel J. Cameron, and Jessica A. Grahn. Using Convolutional Neural Networks to Recognize Rhythm.
Sun, Yi, Yuheng Chen, Xiaogang Wang, and Xiaoou Tang. "Deep learning face representation by joint identification-verification." In Advances in Neural Information Processing Systems, pp. 1988-1996. 2014.
Tantawi, M.; Salem, A.; Tolba, M. F.:Fiducial Based Approach to ECG Biometrics Using Limited Fiducial Points. In: Advanced Machine Learning Technologies and Applications Communications in Computer and Information Science, vol. 488, pp. 199-210 (2014).
Wang L. M.S. Thesis. Shan Dong University; Jinan, China: 2005. The Research Based on the ECG Human Identification Technology.
Zheng, Yi, Qi Liu, Enhong Chen, Yong Ge, and J. Leon Zhao. "Time series classification using multi-channels deep convolutional neural networks." In Web-Age Information Management, pp. 298-310. Springer International Publishing, 2014.

* cited by examiner

MULTI-MODAL BIOMETRIC IDENTIFICATION

CROSS-REFERENCE TO RELATED APPLICATION(S)

The present application is a continuation of U.S. patent application Ser. No. 14/869,088 filed on Sep. 29, 2015, the content of which is hereby incorporated by reference in its entirety.

FIELD OF THE DISCLOSURE

This disclosure relates in general to using multiple biometric signals to identify a unique individual.

BACKGROUND

Biometric characteristics have been used to identify a unique individual for various purposes, including but not limited to access control. The characteristics conventionally include fingerprints, DNA, eye retinas, facial recognition, etc.

SUMMARY

Conventional uses of biometric characteristics for identification are time-consuming and/or require specialized equipment. This limits their use for real-time applications at any number of locations where there may be a desire to identify a unique individual.

The teachings herein may be used with a device worn by an individual that confirms the unique identity of the individual using multi-modal biometric identification. In this way, biometric characteristics can be used in a wide variety of applications in a speedy manner without the use of complicated and/or expensive specialized equipment at use locations.

According to one aspect of the teachings herein, a method includes receiving, at a computing device, at least two biometric measurement signals generated by contact with a single individual, wherein the at least two biometric measurement signals comprise an electrocardiograph (ECG) signal and a photoplethysmography (PPG) signal; combining at least one feature extracted from each signal of the at least two biometric measurement signals to generate a combined biometric signal; comparing the combined biometric signal with a defined biometric signal associated with a known individual; and transmitting a signal, responsive to the combined biometric signal matching the defined biometric signal, indicating that the single individual is the known individual.

According to another aspect of the teachings herein, a method includes receiving, at a computing device, at least two biometric measurement signals generated by contact with a single individual, wherein the at least two biometric measurement signals comprise an electrocardiograph (ECG) signal and a photoplethysmography (PPG) signal; generating a combined biometric signal by combining the at least two biometric measurement signals; comparing the combined biometric signal with a defined biometric signal associated with a known individual; and transmitting a signal, responsive to the combined biometric signal matching the defined biometric signal, indicating that the single individual is the known individual.

According to another aspect of the teachings herein, a method includes receiving, at a computing device, at least two biometric measurement signals generated by contact with a single individual, wherein the at least two biometric measurement signals comprise an electrocardiograph (ECG) signal and a photoplethysmography (PPG) signal; generating a combined biometric signal by combining the at least two biometric measurement signals; comparing the combined biometric signal with a defined biometric signal associated with a known individual; and transmitting a signal, responsive to the combined biometric signal matching the defined biometric signal, indicating that the single individual is the known individual.

According to another aspect of the teachings herein, an apparatus includes a non-transitory memory; and a processor configured to execute instructions stored in the non-transitory memory to receive, at a computing device, at least two biometric measurement signals generated by contact with a single individual, wherein the at least two biometric measurement signals comprise an electrocardiograph (ECG) signal and a photoplethysmography (PPG) signal; generate a combined biometric signal by combining the at least two biometric measurement signals; compare the combined biometric signal with a defined biometric signal associated with a known individual; and transmit a signal, responsive to the combined biometric signal matching the defined biometric signal, indicating that the single individual is the known individual.

According to another aspect of the teachings herein, an apparatus includes a body having at least two surfaces, an electrocardiogram (ECG) sensor including a first electrode coupled to a first surface of the body and a second electrode coupled to a second surface of the body such that a single lead ECG is formed by contact of a first portion of an individual with the first electrode and a second portion of the individual with the second electrode, a photoplethysmography (PPG) sensor on one of the at least two surfaces electrically coupled to the ECG sensor so as to activate responsive to forming the single lead ECG, and at least one communication device coupled to the body and controlled by a processor to wirelessly transmit biometric measurement signals from each of the ECG sensor and the PPG sensor to an external server, wirelessly receive a first signal from the external server indicative of biometric identification data generated from the biometric measurement signals, and wirelessly transmit a second signal to an identification device responsive to a match between the biometric identification data generated from the biometric measurement signals and biometric identification data of a known individual.

Another apparatus described herein includes a non-transitory memory and a processor. The processor is configured to execute instructions stored in the memory to receive at least two biometric measurement signals generated by contact with a single individual, extract at least one feature from each signal of the at least two biometric measurement signals, combine the at least one feature extracted from each signal to generate a combined biometric signal, compare the combined biometric signal with a defined biometric signal associated with a known individual, and transmit a signal, responsive to the combined biometric signal matching the defined biometric signal, indicating that the single individual is the known individual.

Details of these implementations, modifications of these implementations, and additional implementations are described below.

BRIEF DESCRIPTION OF THE DRAWINGS

The description herein makes reference to the accompanying drawings wherein like reference numerals refer to like parts throughout the several views, and wherein.

DETAILED DESCRIPTION

In order to uniquely identify an individual using a biometric characteristic, that characteristic is universal, easily measured, unique and permanent. That is, a universal biometric characteristic is one that each individual possesses. It is easily measured if, e.g., it is technically easy and convenient for the individual to obtain a measurement of the characteristic. Ideally, the biometric characteristic is unique in that no two individuals have identical measurements for the characteristic and is permanent in that the characteristic does not change over time.

One possible biometric identification system can rely upon an echocardiogram (ECG). However, such a system presents many technical challenges. One challenge is that the shape of an ECG changes with heart rate. Moreover, ECGs are often noisy due to changes in an individual's position during measurement. ECG morphologies also vary within an individual and a population, making a common measurement system challenging to implement. For example, ECG morphology may be different for users with or without cardiac symptoms. As another challenge, roughly 5% of the population has a non-pronounced Lead I ECG— that is, a single lead ECG output produces features that are difficult to extract and hence presents difficulties in identifying an individual.

For the foregoing reasons, the use of an ECG alone is not accurate enough to guarantee that an individual is correctly identified. Such use could also potentially confuse users with similar ECG morphology.

In contrast, the identification described herein combines multiple different biometric signals from respective sensors. Such a multi-model biometric system increases accuracy and specificity over using a single biometric signal.

Figure 1:
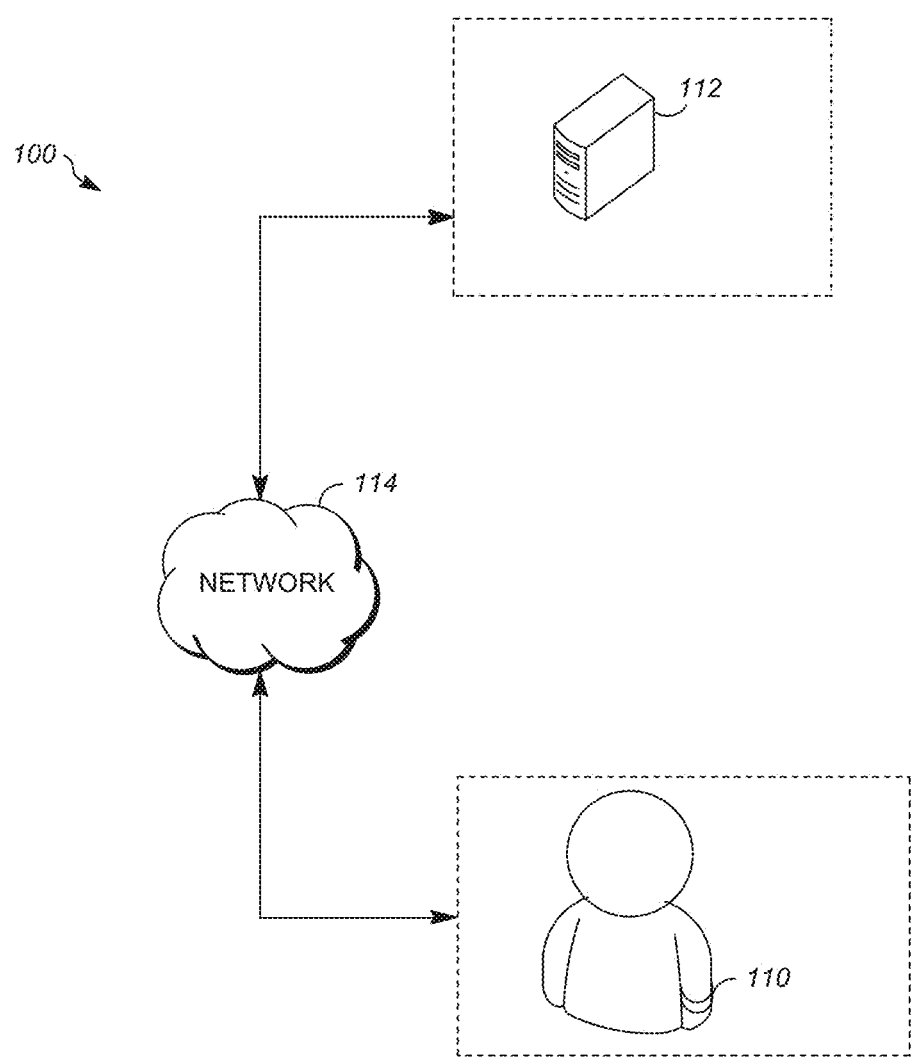
FIG. 1 is a diagram showing an example of a system configuration for a biometric identification device and server that may be used according to implementations of this disclosure.

FIG. 1 is a diagram showing an example of a system configuration 100 for a biometric identification device 110 and server 112 that may be used in implementations of this disclosure.

Biometric identification device 110 as shown is a wearable biometric identification device, namely a device worn around an individual's wrist. However, other devices can be used. For example, device 110 could instead be implemented by another wearable device such as a ring or necklace. Alternatively, device 110 could be implemented as another portable device that is configured to travel with an individual, but not be worn by the individual, such as a device similar in form to a key fob.

Figure 2A:
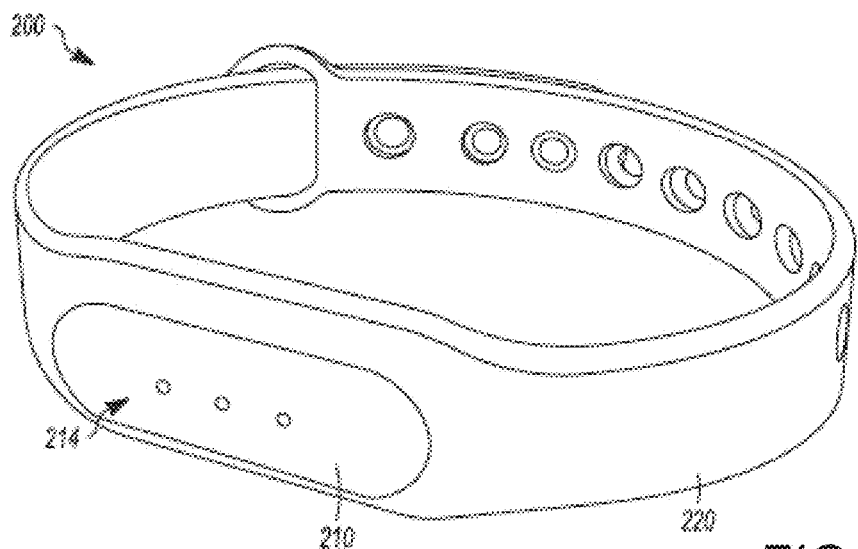
FIG. 2A is an illustration showing a perspective view of one example of a wearable biometric identification device according to an implementation of this disclosure.
Figure 2B:
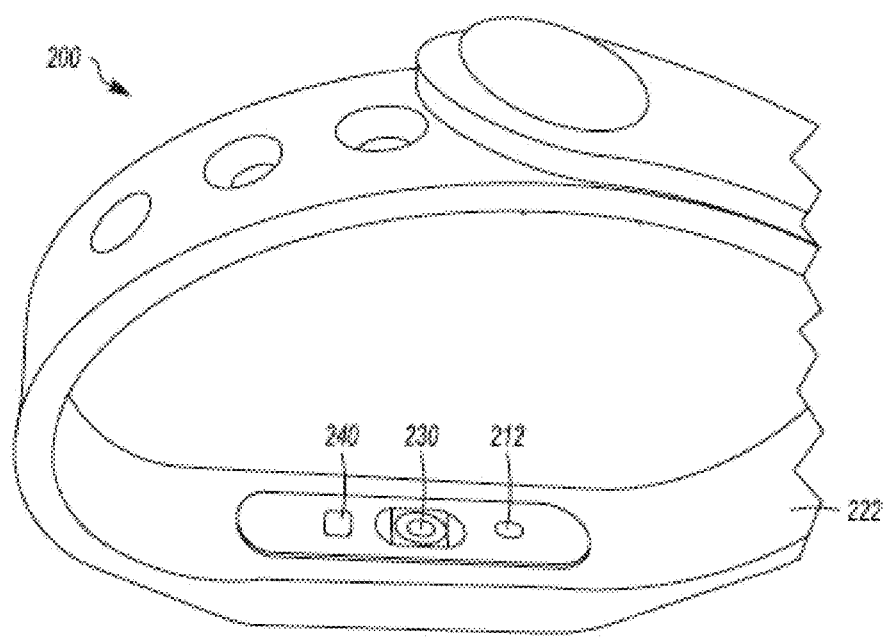
FIG. 2B is an illustration showing another perspective view of the example of the wearable biometric identification device according to FIG. 2A.

A configuration of biometric identification device 110 is described in more detail with reference to FIGS. 2A, 2B and 3. Referring first to FIGS. 2A and 2B, biometric identification device 110 is a wearable wrist device 200. Although device 200 is shown as having a single, continuous body joined at opposite ends by a single fastener, other structures wearable on or around an individual's wrist may be used.

Device 200 includes an electrocardiogram (ECG) component comprising first and second electrodes 210 and 212 configured to measure various aspects of the individual's heart function and related biometrics. First electrode 210 is coupled to an exterior surface 220 and is not in direct contact with the individual that is wearing device 200. Second electrode 212 is coupled to an interior surface 222 facing skin of the individual that is wearing device 200, in this case the individual's wrist. Second electrode 212 may or may not be in contact with the wrist at all times when device 200 is worn. First electrode 210 and second electrode 212 are configured to identify electrical heart activity by measuring the user's pulse and transmitting the measurement data for subsequent encoding and processing. That is, upon the individual contacting first electrode 210, for example with a finger, the second electrode 212, if not already in contact with the individual's skin, contacts the skin to form a single lead ECG sensor 214, which permits device 200 to measure the individual's heart activity as discussed in more detail hereinafter.

Additionally included with device 200 is a photoplethysmography (PPG) component or sensor 230. PPG signals from PPG sensor 230 may be used to estimate skin blood flow using infrared light as discussed in more detail herein. Although not shown in detail for clarity, PPG sensor 230 is generally supported on a printed circuit board (PCB) mounted interior of device 200 that also includes other circuitry such as a microcontroller, battery management, and LED circuits. The circuitry controls the external components of PPG sensor 230, which include a light emitter and at least one photodetector spaced apart on interior surface 222. The light emitter transmits red and infrared lights originating from red and infrared light emitting diodes through the individual's skin, which lights are received by the photodetector. Upon receipt, the photodetector transmits the measurement data for subsequent encoding and processing. Unlike with ECG sensor 214, which requires completion of a circuit between first electrode 210 and second electrode 212, PPG sensor 230 does not require an additional step beyond wearing device 200 to take its measurements. In a desirable implementation, however, PPG sensor 230 is operatively connected to ECG sensor 214 so that completion of the circuit between first electrode 210 and second electrode 212 also sends a signal according to any known technique to monitor and measure the individual's skin blood flow.

Although not required, device 200 may include other components not expressly shown. For example, further sensor components generating biometric signals through non-invasive techniques may be included within device 200. It will be apparent to one skilled in the art in view of this disclosure that the disposition of the further sensor components within or on device 200 will depend on their specific nature, e.g., whether a component can function only by contact with the skin of the individual, whether one or more contacts are needed, etc.

As another example, device 200 may include display components. One display component may be an LED indicator that emits light when biometric identification data is being collected. Another may be a display configured to visually represent collected biometric identification data. In an implementation, the display may be a single output screen for visually representing all collected biometric identification data. In another implementation, the display may be a plurality of output screens wherein each output screen visually represents a unique type of collected biometric identification data. In another implementation, the display may be a plurality of output screens wherein any collected biometric identification data may be visually represented on any such display. The information outputted to a display may be updated as biometric identification data is processed.

As mentioned, the photodetector of PPG sensor 230 may transmit measurement data for subsequent encoding and processing. Similarly, the ECG sensor may transmit its measurement data. In the example of FIGS. 2A and 2B, this transmission may be achieved by a communication component 240. Communication component 240 permits device 200 to communicate with one or more external systems or devices, for example, to transmit biometric identification data collected by device 200. As will be discussed in greater detail below, communication component 240 may assist a user by transmitting biometric identification data to a server for review or comparison against newer collected measurements as historical data. In an embodiment, communication component 240 is a Bluetooth transmitter; however, communication component 240 may operate over other suitable wireless communication systems, including without limitation an ultrasound transmitter. Accordingly, communication component 240 may receive incoming signals verifying an individual's identity. Communication component 240, or a separate communication component, may transmit a wireless signal upon verification of the individual's identity. For example, this verification may be achieved by a microchip that is attached to an antenna (the microchip and the antenna together are called an RFID transponder or an RFID tag). The antenna allows the chip to transmit the identification information to a reader remote of the individual. The reader converts the radio waves reflected back from the RFID tag into digital information that can then be passed on to computers for use in registering purchases, allowing entry through a security door, etc., based on the identification of the individual.

Referring again to FIG. 1, server 112 may be implemented by any configuration of one or more computers, such as remote server computers. For example, certain of the operations described herein may be performed by a server computer in the form of multiple groups of server computers that are at different geographic locations and may or may not communicate with one another, such as by way of network 120. While certain operations may be shared by multiple computers, in some implementations different computers are assigned different operations. For example, one or more servers 112 could be used to process biometric identification data as described hereinafter, and transmit a signal to the biometric identification device 110 and/or elsewhere confirming or denying a match, while one or more different servers 112 may receive signals from, for example, a remote reader when the identity of the individual carrying or wearing the biometric identification device 110 is confirmed. The remote reader itself may also be a computer or part of a computer.

Network 150 can be one or more communications networks of any suitable type in any combination, including wireless networks, wired networks, local area networks, wide area networks, cellular data networks and the Internet. Biometric identification device 110 and server 112 can communicate with each other via network 120. In the implementations described herein, one network 150 is shown. Where more than one server 112 is used in an implementation, each server 112 may be connected to the same network 150 or to different networks 150.

Figure 3:
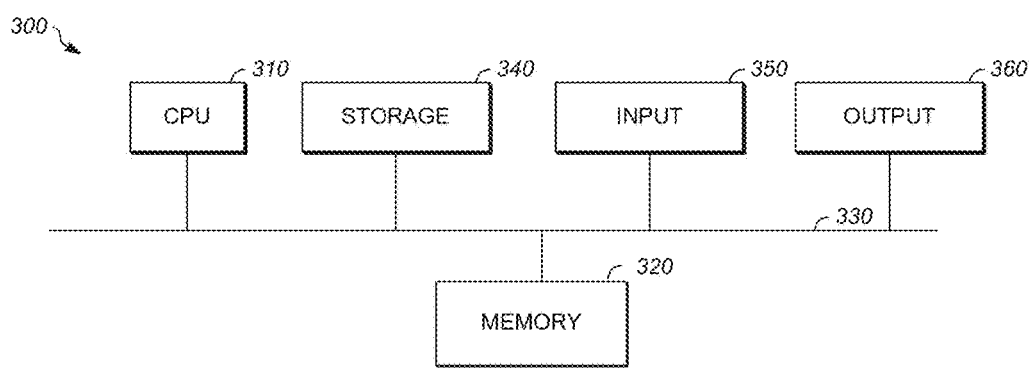
FIG. 3 is a diagram showing an example of a hardware configuration for a biometric identification device and/or a server that may be used according to implementations of this disclosure.

FIG. 3 is a diagram showing an example of a hardware configuration 300 for a biometric identification device and/or a server that may be used according to implementations of this disclosure. For example, one or more servers 112 could be implemented using hardware configuration 300.

Hardware configuration 300 can include at least one processor such as a central processing unit (CPU) 310. Alternatively, CPU 310 can be any other type of device, or multiple devices, capable of manipulating or processing information now-existing or hereafter developed. Although the examples herein can be practiced with a single processor as shown, advantages in speed and efficiency may be achieved using more than one processor.

Memory 320, such as a random access memory device (RAM) or any other suitable type of non-transitory storage device, stores code and data that can be accessed by CPU 310 using a bus 330. The code may include an operating system and one or more application programs manipulating and/or outputting the data. As will be discussed in detail below, an application program can include software components in the form of computer executable program instructions that cause CPU 310 to perform some or all of the operations and methods described herein. When hardware configuration 300 is used to implement server 112, for example, an application program stored by memory 320 may implement some or all of a process according to FIG. 4 as described in more detail below.

Hardware configuration 300 may optionally include a storage device 340 in the form of any suitable non-transitory computer readable medium, such as a hard disc drive, a memory device, a flash drive or an optical drive. Storage device 340, when present, provides additional memory when high processing requirements exist.

Hardware configuration 300 includes one or more input devices 350, such as a keyboard, a mouse, a microphone or a gesture-sensitive input device. Through an input device 350, data may be input from a user. For example, a gesture-sensitive input device may receive different gestures to switch between different display modes (e.g., heart rate, time, ECG). Any other type of input device 350, including an input device not requiring user intervention, is possible. For example, input device 350 may be a communication device such as a wireless receiver operating according to any wireless protocol for receiving input signals from biometric identification device 110 when hardware configuration 300 is used to implement server 112. Input device 350 can output signals or data indicative of the inputs to CPU 310, e.g., along bus 330.

Hardware configuration 300 also includes one or more output devices 360. Output device 360 may be a display or a speaker. If output device is a display, for example, it may be a liquid crystal display (LCD), a cathode-ray tube (CRT), or any other output device capable of providing visible output to an individual. In some cases, an output device 360 may also function as an input device 350—a touch screen display configured to receive touch-based input, for example. Output device 360 may alternatively or additionally be formed of a communication device for transmitting signals. For example, output device 360 may include a wireless transmitter using a protocol compatible with a wireless receiver of biometric identification device 110 to transmit signals from server 112 to biometric identification device 110.

Although FIG. 3 depicts one hardware configuration 300 that can implement server 112, other configurations can be utilized. The operations of CPU 310 can be distributed across multiple machines or devices (each machine or device having one or more of processors) that can be coupled directly or across a local area or other network. Memories 320 can be distributed across multiple machines or devices such as network-based memory or memory in multiple machines performing operations that may be described herein as being performed using a single computer or computing device for ease of explanation. Although a single bus 330 is depicted, multiple buses can be utilized. Further, storage device 340 can be a component of hardware configuration 300 or can be a shared device that is accessed via a network. The hardware configuration of a computing system as depicted in an example in FIG. 3 thus be implemented in a wide variety of configurations.

The hardware configuration of one biometric identification device 110 is described with reference to device 200 of FIGS. 2A and 2B. A more generalized configuration is represented by hardware configuration 300. For example, hardware configuration 300 may implement at biometric identification device 110 where input devices 350 are a plurality of biometric measuring devices including but not limited to ECG component or sensor 214 and PPG component or sensor 230 described with reference to FIGS. 2A and 2B. Input devices 350 may also include a communication component, such as a wireless receiver, either alone or combined with a corresponding output device 360, such as a wireless transmitter.

Figure 4:
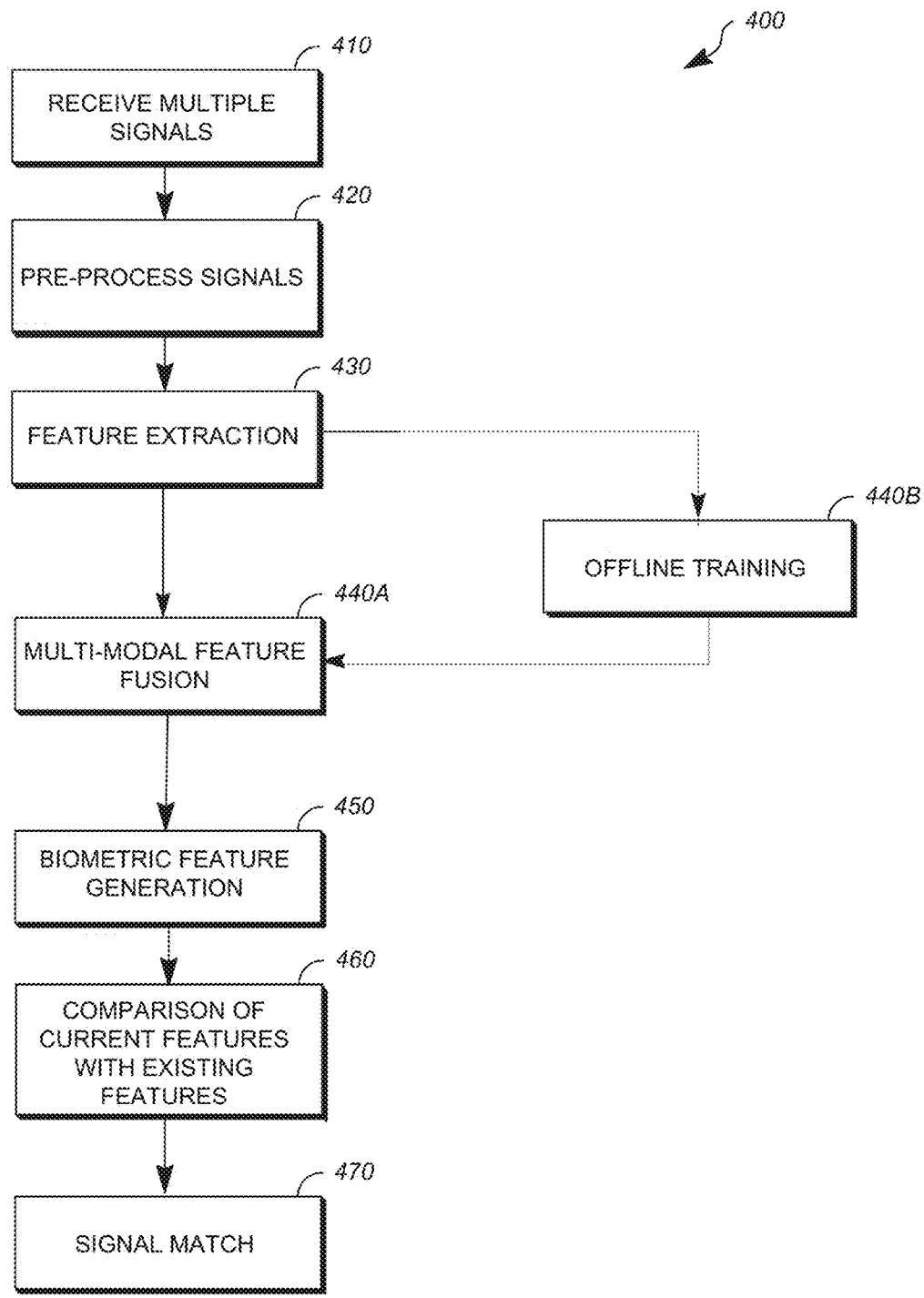
FIG. 4 is a flow chart showing an example of a process overview of biometric identification processing according to implementations of this disclosure.

FIG. 4 is a flow chart showing an example of a process or method 400 for processing biometric data collected from a biometric identification device 110. The operations described in connection with method 400 can be performed at one or more computing devices, such as device 110 or server 112. When an operation is performed by one or more such computing devices, it is completed when it is performed by one such computing device. The operations described in connection with method 400 can be embodied as a storage device in the form of a non-transitory computer readable storage medium including program instructions executable by one or more processors that, when executed, cause the one or more processors to perform the operations. For example, the operations described in connection with method 400 could be an application program stored at memory 320 and be executable by CPU 310.

At operation 310, biometric measurement signals from at least two biometric sensors are received. The biometric measurement signals may be collected as biometric measurement data from the sensors. In this example, the biometric measurement signals include at least ECG signals and PPG signals, so the biometric sensors include at least an ECG sensor and a PPG sensor such as ECG sensor 214 and PPG sensor 230 shown in FIGS. 2A and 2B. In operation, the sensors may be activated to begin measurements by a variety of techniques. For example, an individual wearing biometric identification device 200 can contact first electrode 210 so as to complete a circuit with second electrode 212 to produce measurement data from ECG sensor 214. Contact may be made by touching first electrode 210 with a finger from a hand other than the hand wearing biometric identification device 200. Second electrode 212 is either in contact with the individual at all times or is pressed into contact therewith by the finger. That completed circuit can, in turn, activate PPG sensor 230 to produce measurement data from PPG sensor 230. In this way, biometric identification device 110 receives biometric measurement signals.

Method 400 may be performed in whole or in part by biometric identification device 110. In this example, however, method 400 is performed by server 112. Accordingly, the biometric measurement signals may be received at server 112 from biometric identification device 110 through, for example, a wireless communication component in operation 410. Also in this example, only ECG and PPG signals are discussed, but other biometric measurement signals would be subject to the same processing. In some implementations, measuring biometric signals ends after a defined period of time lapses. In other implementations, measuring biometric signals ends when contact of the individual with first electrode 210 ends—breaking the circuit formed with second electrode 212. It is also possible that the period for measuring some biometric signals is longer than the period for measuring other biometric signals and/or these techniques are combined. For example, ECG sensor 214 obtains measurements only while contact is maintained by the individual with first electrode 210, and PPG sensor 230 obtains measurements for a predetermined time period after activation.

At operation 420, the ECG signals and PPG signals separately undergo signal pre-processing to prepare the subsequent analysis. Pre-processing encompasses a number of manipulations to the signals to ensure data integrity and prepare the signals for feature extraction at operation 430. The type of pre-processing varies according to the type of signal, but it generally involves denoising of the raw signals from the sensors. Pre-processing may include, for example, removing baseline wander in the signals. This processing generally adjusts the input signals during one measurement cycle to a common baseline. Filtering, such as using a band pass filter, may be applied in order to remove any undesirable data shifts that occurred while the signals were being measured and to reduce the presence of data outside of a range to be observed (e.g., outliers). While the biometric signals from different sensors are processed separately, comparisons between them may be useful for processing each signal. For example, where different signals each derive from the individual's pulse measurement, the periodicity of the measured signals is likely to be equal or substantially equal. To the extent they are not, this may indicate motion noise within one or the other of the signals. Motion noise may include, for example, fluxes and other changes present in ECG and PPG signals due to the user walking, running, exercising, or otherwise moving in a manner that may interfere with a clear biometric measurement (e.g., where the user's contact with first electrode 210 moves while ECG signals are being measured). The differences may be used in a filtering process for motion noise.

At operation 430, feature extraction occurs on each respective pre-processed signal. There is more than one approach for feature extraction that may be used in operation 430. In general, a fiducial point based approach (also called a rule based approach) detects values associated with various segments of a signal, while an appearance based approach detects the shapes of the signal. It can be the shape in the time domain, such as a wave fragment, or the shape in the frequency domain, for example, the output from the combination of autocorrelation and discrete cosine transform of the signal. The fiducial point based approach is described with reference to FIGS. 5 and 6, while the appearance based approach is described with reference to FIGS. 7A-7D and 8.

Figure 5:
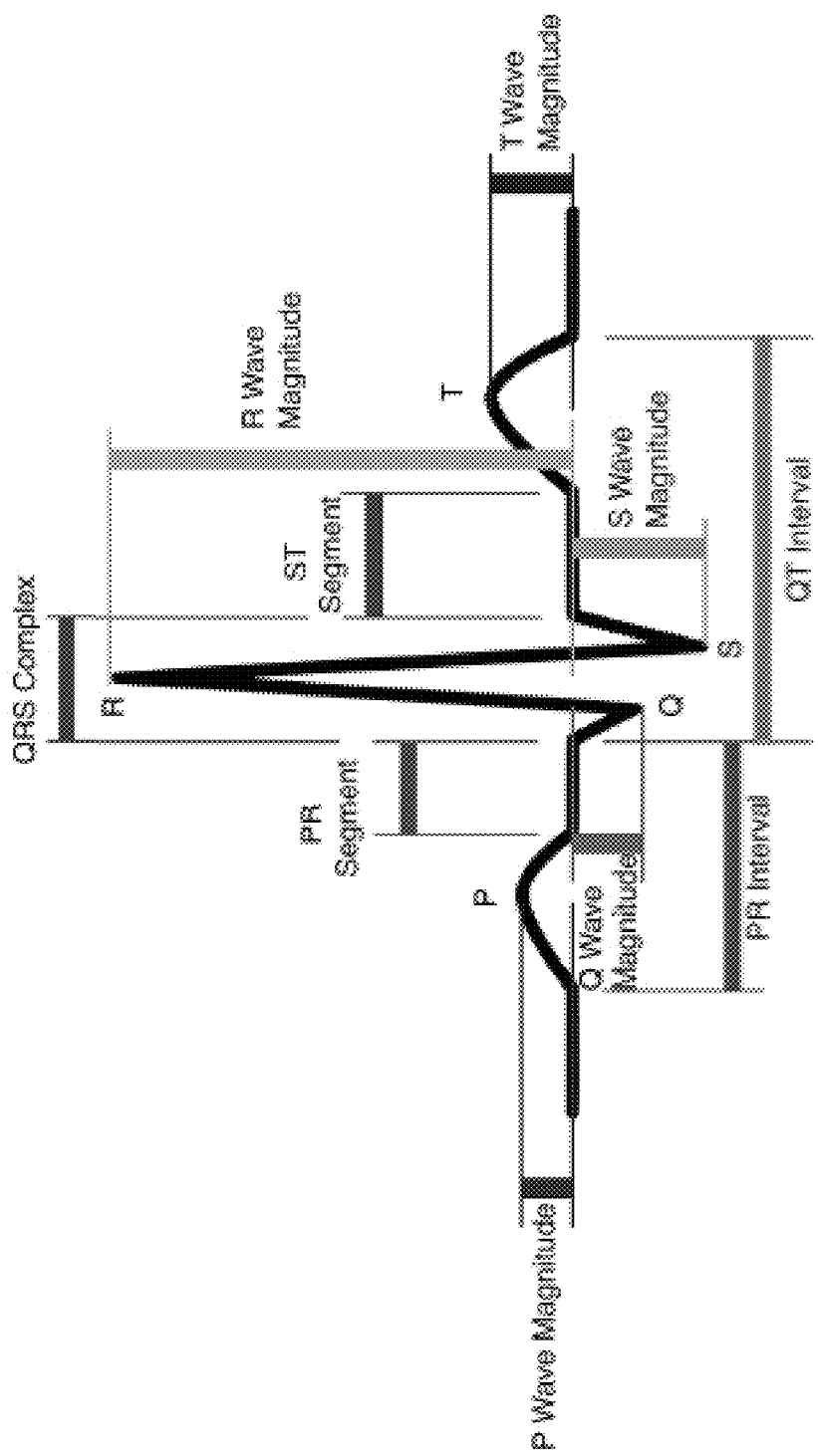
FIG. 5 is a graph of a hypothetical output of an ECG sensor over time with a number of fiducial points illustrated.

FIG. 5 is a graph of a hypothetical output of an ECG sensor over time with a number of fiducial points illustrated. The output of FIG. 5 is assumed to be a pre-processed signal resulting from operation 420 and is idealized as seen by the flat baseline. The output curve generally represents voltage over time, but any appropriate measurement unit may be used. A typical ECG output is a repeating cycle formed of a P wave (representing atrial depolarization), a QRS complex (representing ventricular depolarization) and a T wave (representing ventricular repolarization). A PR segment exists from the end of the P wave to the beginning of the QRS complex, and an ST segment exists from the end of the QRS complex to the beginning of the T wave. Other electrical entities may be represented in an ECG output.

Each of these electrical entities within an ECG curve is associated with one or more amplitudes (used interchangeably with magnitude herein unless otherwise noted) and one or more time intervals or durations. For example, in the QRS complex, Q and S are valleys and R is a peak, each associated with a different amplitude. The amplitude of any point within can be either an absolute amplitude (measured relative to the baseline) or a relative amplitude (measured as compared to another amplitude). Using absolute measurements, for example, FIG. 5 shows that valley Q has a Q wave magnitude, peak R has an R wave magnitude, and valley S has an S wave magnitude. The magnitude of the T wave and the magnitude of the P wave are also shown in FIG. 5. An interval or duration may be measured from any point in the repeating cycle to any other point. For example, the individual may be represented by a PR interval from the start of the P wave to the start of the QRS complex and a QT interval from the start of the QRS complex to the end of the T wave.

Using the fiducial based approach, feature extraction in FIG. 5 involves detecting or calculating at least some of the durations/intervals and at least some of the amplitudes/magnitudes within the ECG curve or waveform. Feature extraction may be achieved using calculations including one or more of a spectral based feature, wavelet, discrete cosine transformation (DCT), power density, Ensemble Empirical Mode Decomposition (EEMD). The features could be the amplitude and duration values themselves, combinations of the amplitude and/or duration values or values derived using the amplitude and/or duration values through, for example, Autocorrelation Coefficient (AC) or a Periodicity Transform (PT). One feature may be, for example, heart rate variability (HRV), which is the variation of beat-to-beat intervals (i.e., the time from R to R per cycle). The features may be reduced or encoded using principal component analysis (PCA), latent discriminant analysis (LDA) and/or independent component analysis (ICA).

Figure 6:
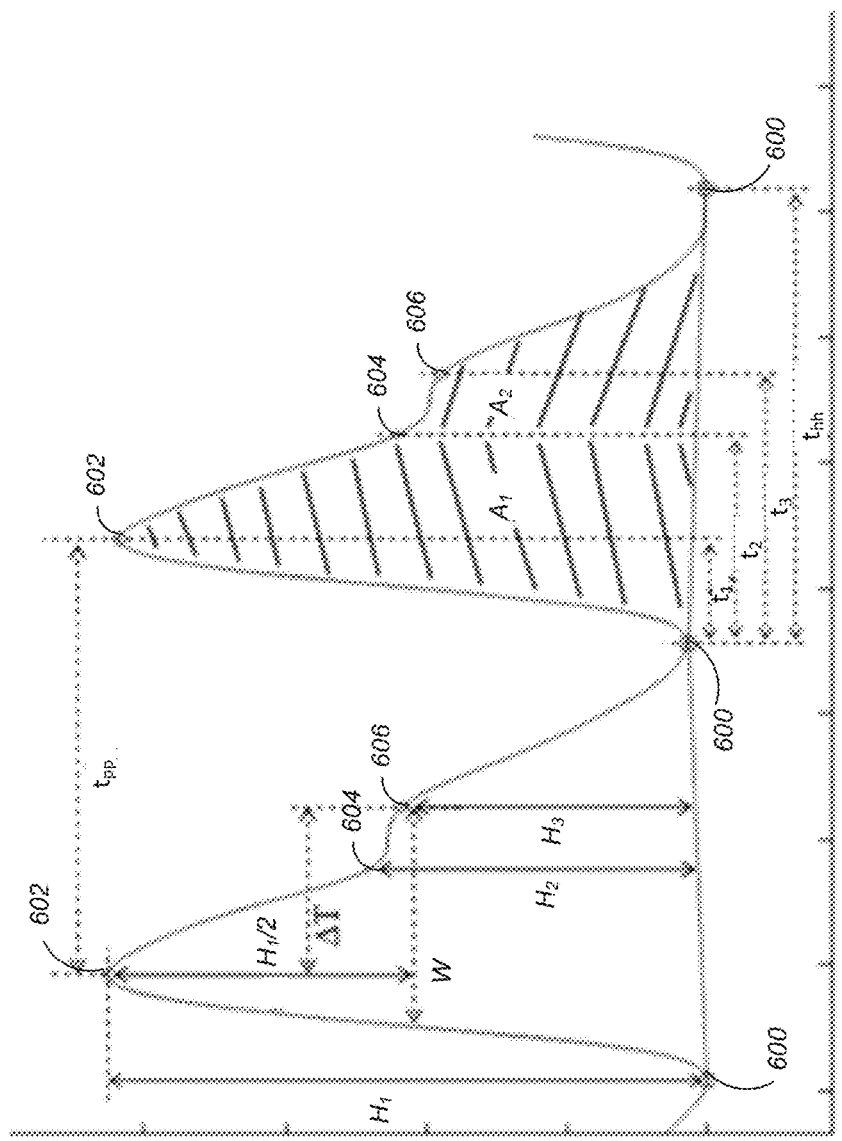
FIG. 6 is a graph of a hypothetical output of a PPG sensor over time with a number of fiducial points illustrated.

FIG. 6 is a graph of a hypothetical output of a PPG sensor over time with a number of fiducial points illustrated. It is based on FIG. 7 in Reş it Kaysaoğlu et al., "A novel feature ranking algorithm for biometric recognition with PPG signals," Computers in Biology and Medicine 49 (2014). The output of FIG. 6 is assumed to be a pre-processed PPG signal resulting from operation 420. A typical PPG output is a repeating cycle that can have various forms other than that shown by example in FIG. 6, which is idealized for illustration purposes. Like FIG. 5, the x-axis represents time (e.g., in seconds). Here, the y-axis is per-unit amplitude.

The PPG signal of FIG. 6 has a number of fiducial points useful for identification that can be extracted at operation 430. In a cycle, the highest point reached after a hole 600 (a baseline value) is a systolic peak 602 at amplitude $H_1$. The dicrotic notch 604 has an amplitude $H_2$, and the diastolic peak 606 has an amplitude $H_3$. The diastolic peak 606 is ideally located at half of the amplitude $H_1/2$, but it may not be in practice. In any event the width W of the cycle is measured at amplitude $H_1/2$. Time periods or durations also provide desirable data for feature extraction. The time duration $t_{pp}$ is measured between adjacent systolic peaks 602, while the time duration $t_{hh}$ is measured between adjacent holes 600. Some other time durations shown include time duration $t_1$ between a hole 600 and a systolic peak 602, time duration $t_2$ between the systolic peak 602 and a dicrotic notch 604, and time duration $t_3$ between the dicrotic notch 604 and a diastolic peak 606. The area under each portion of the cycle may be a feature extracted from the points of FIG. 6. In FIG. 6, area $A_1$ represents the area under the curve defined by a systolic peak 602 between a hole 600 and a dicrotic notch 604, while area $A_2$ represents the area under the curve defined by the diastolic peak 606 between a dicrotic notch 604 and a hole 600. Accordingly, feature extraction in FIG. 6 using the fiducial based approach involves detecting or calculating at least some of the durations $t_1$, $t_2$, $t_3$, $t_{pp}$, and $t_{hh}$ and at least some of the amplitudes $H_1$, $H_2$, and $H_3$.

FIGS. 7A-7D are graphs used to describe a frequency domain, appearance based approach to feature extraction. The processing of FIGS. 7A-7D is described with respect to an ECG signal only, but similar processing would apply to any cyclical biometric input signal, including a PPG signal. Moreover, the processing of FIGS. 7A-7D is one example of an appearance based approach—others that analyze the cyclical nature of the signal without the specific identification of multiple fiducial points within the signal are also possible given the teachings herein.

Figure 7A:
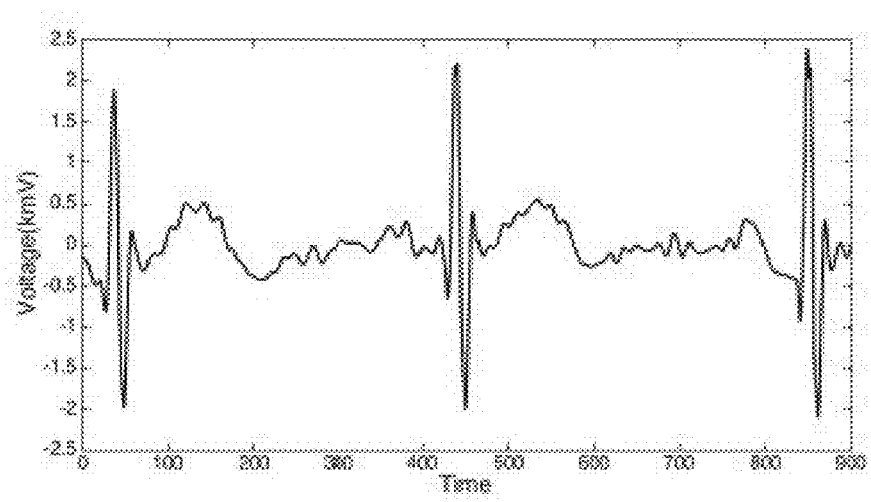
FIGS. 7A-7D are graphs used to describe a frequency domain, appearance based approach to feature extraction.
Figure 7B:
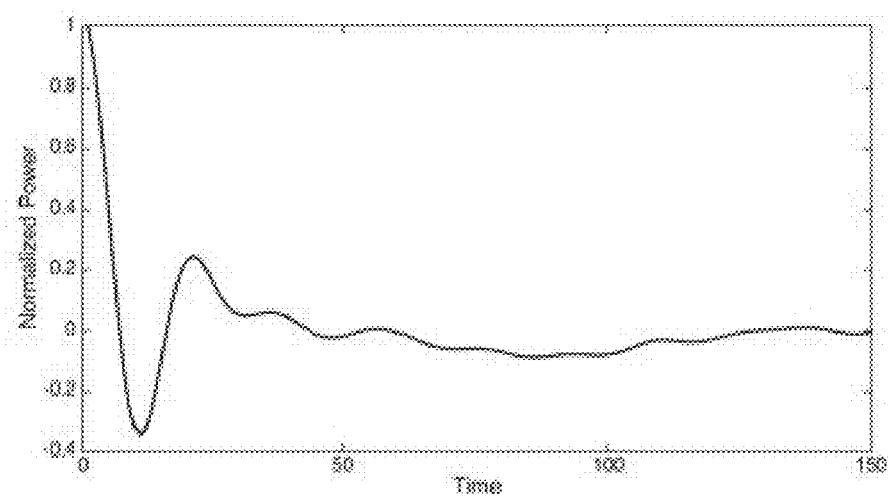
Figure 7C:
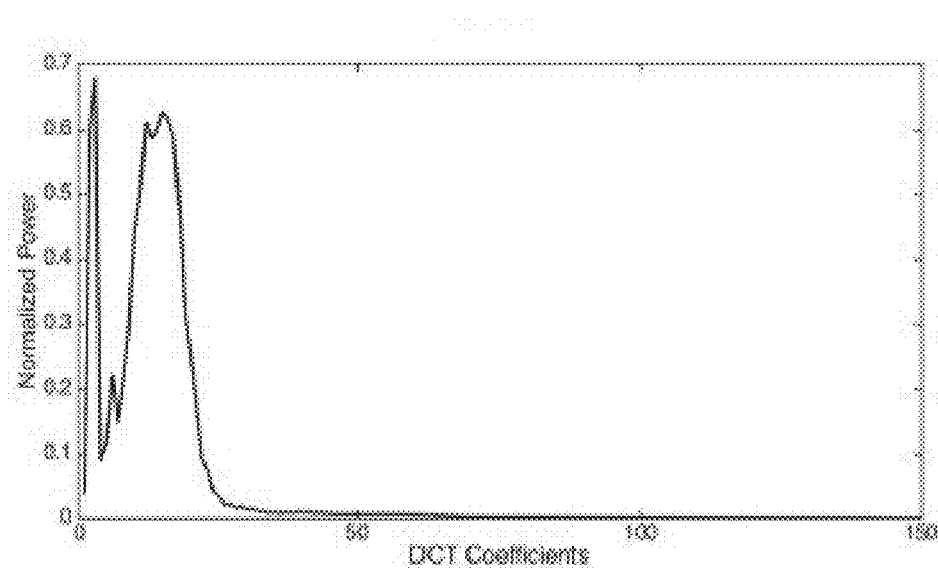
Figure 7D:
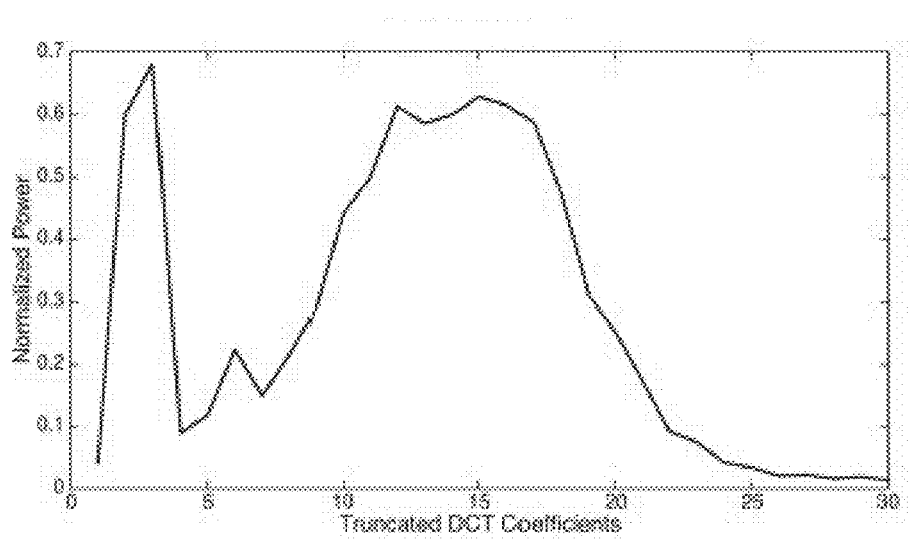

FIG. 7A is a graph of voltage versus time, which represents three seconds of an ECG signal from a person. The output of FIG. 7A is assumed to be a pre-processed ECG signal resulting from operation 420. Feature extraction at operation 430 in this case is a four-step process that begins with windowing, where the pre-processed ECG signal or trace is segmented into non-overlapping windows so that each window has a length sufficient to encompass multiple cycles. For example, each window for the signal of FIG. 7A should be longer than the average heartbeat length so that multiple pulses are included. Next, autocorrelation is performed so as to estimate the normalized autocorrelation of each window. Doing so to the signal of FIG. 7A extending for several more cycles results in the graph of FIG. 7B, which is a zoomed plot of the power versus signal time after autocorrelation. Once autocorrelation is completed, a discrete cosine transform over L lags of the autocorrelated signal is performed, where L is a positive integer. FIG. 7C is a DCT plot of the power of the resulting DCT coefficients. FIG. 7D is a zoomed DCT plot of the power values of truncated DCT coefficients from FIG. 7C. The final step of the feature extraction is classification based on the significant DCT coefficients. For example, the extracted features could include a certain number of the highest DCT coefficients, how many DCT coefficients are associated with certain power values, a fitted curve for the points defining peaks or valleys in the DCT plot, etc.

Figure 8:
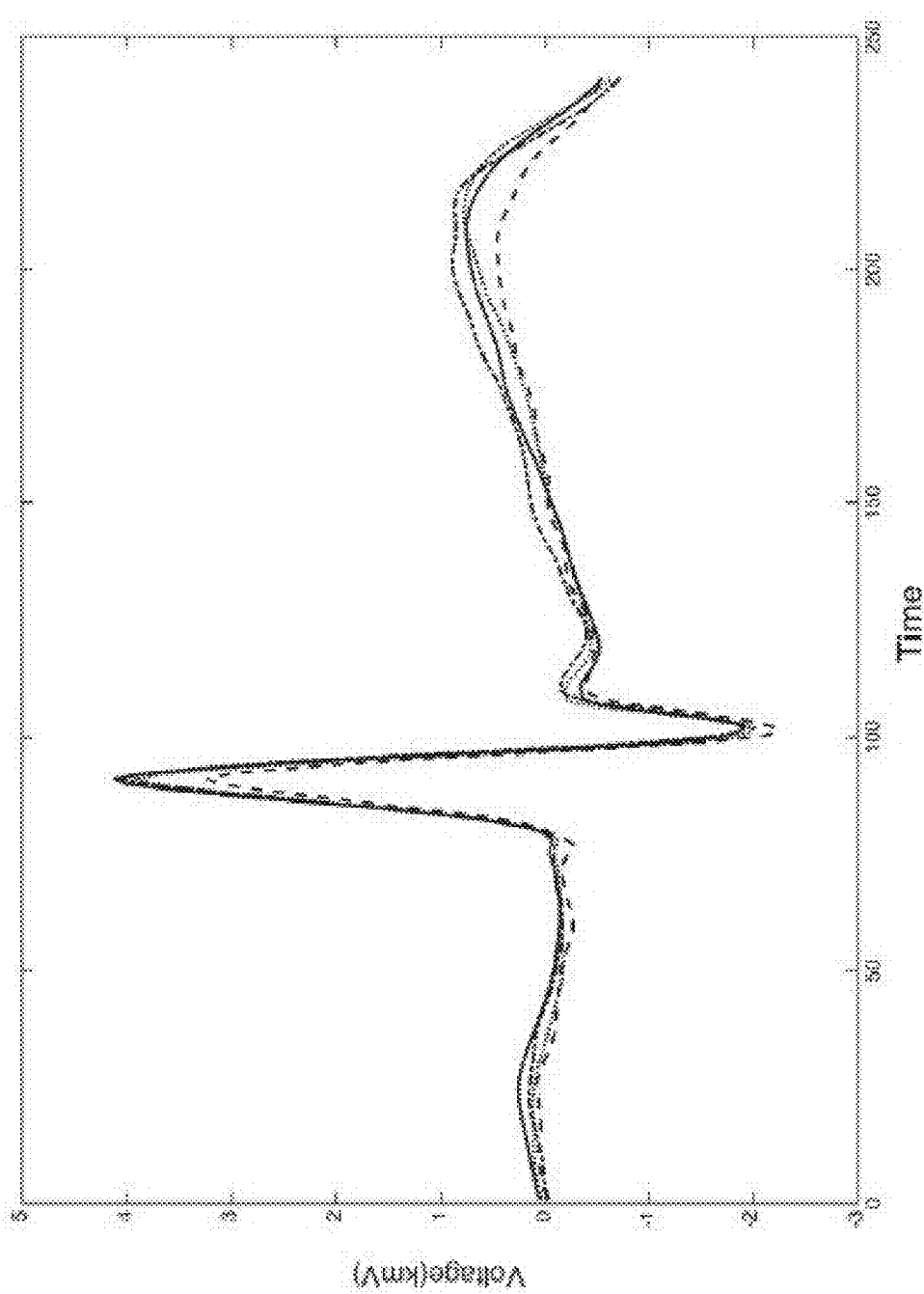
FIG. 8 is a graph used to describe a time domain, appearance based approach to feature extraction.

FIG. 8 is a graph used to describe a time domain, appearance based approach to feature extraction. The time domain, appearance based approach to feature extraction may involve, for example, extracting PQRST fragments for characterization of an individual. This extraction involves, first, superimposing samples of an ECG sensor output over time by synchronizing their peaks R. Then, a uniform fragment length for the PQRST fragments is selected. The PQRST fragments are intended to capture at least the entirety of a cardiac cycle from the start of a P wave to the end of a T wave. Because the intervals within the cycle are not constant, the uniform fragment length may be selected by detecting the peak R and selecting a constant number of samples from the output of the ECG sensor before the peak R and a constant number of samples from the output of the ECG sensor after the peak R. The number of samples before the peak R and the number of samples after the peak R used to generate the PQRST fragments may be different. After extraction, the PQRST fragments may be further processed to minimize dissimilarities to the extent they remain after pre-processing at 420. For example, the fragments may be adjusted vertically due to baseline drift, some fragments may be filtered out due to distortion during measurement (e.g., they are too different from the mean due to motion, etc.), and/or they may be corrected due to variations in heart rate according to known techniques. FIG. 8 illustrates several extracted PQRST fragments after this processing. The fragments of FIG. 8 may then be used for classification, either with or without a reduction in the feature space using PCA, wavelet transformation, etc.

As may be apparent from the foregoing descriptions, approaches to feature extraction each have their strengths and weaknesses. While the fiducial point based approach is well-adjusted to changes in heart rate (e.g., its accuracy does not significantly decrease with heart rate changes), it requires a good detection algorithm, it is slow, and it is sensitive to noise. In contrast, the frequency domain, appearance based approach does not need to detect various segments of the signal, so it is faster. The time domain, appearance based approach only relies on the detection of the peak R of the QRS complex, which is a relatively easier task as compared to the detection of other fiducial points. The appearance based approach is also less sensitive to noise. Thus, and referring again to FIG. 4, feature extraction at operation 430 uses both approaches on each biometric measurement signal to improve accuracy herein. Thus, feature extraction at operation 430 combines the analysis for a single biometric signal.

There are two techniques for combining the two approaches. The first is a feature level combination and the second is a decision level combination. In one example of the feature level combination, features extracted from each approach are produced as the combined output for an input biometric signal. In one example of the decision level combination, thresholds or other tests may be applied to features generated by each approach to select only some of the features as the combined output for an input biometric signal. For example, features from each approach may be selected when a feature falls outside of one or more standard deviations of the values for the feature within a known population. In another example, features that are not likely to be differentiating may be filtered out.

Referring again to FIG. 4, operation 440A or both of operations 440A and 440B may be performed after feature extraction at operation 430. Multi-modal feature fusion in operation 440A combines the features from each of the biometric measurement modes into a common set of data for use in a subsequent biometric identification matching step. In one implementation, the fusion is a learning based feature fusion method that applies weights associated with each modality that are learned through training data to generate biometric features for the individual currently using the biometric identification device 110 for comparison with biometric features of a known owner/user.

Optionally, operation 440B in process 400 may be used for obtaining the data for offline training. More specifically, some or all of the features extracted at operation 430 may be provided to operation 440B to combine with other data for offline training. Operation 440B may be performed by server 112 or elsewhere and may include data for extracted features collected from a relatively large population of individuals as training data. According to one implementation, the training data from the different modalities is ranked using a regression technique, such as Random Forest™ regression. Then, each feature is assigned a weight as a result of the regression. Other learning based methods of feature fusion are also possible, such as a support vector machine (SVM) method, metric learning, etc. Each technique desirably results in a weight that reflects the relative importance of an extracted feature as compared to all features. For example, an extracted feature that is common to a large number of individuals would be less important (and hence be given a lower weight) than an extracted feature that is less common and would provide a better feature for differentiating one individual from the population as a whole.

Regardless of whether the current output of operation 430 is provided for offline training at operation 440B, the weights learned through the training data at operation 440B are used at operation 440A for the multi-modal feature fusion in conjunction with the current data. In one implementation of operation 440A, weights from the offline training 440B are applied to the features extracted at operation 430 to generate data for a comparison at operation 460.

In an initial set up process, the biometric identification device 110 may be associated with an individual by performing operations 410, 420, 430, and optionally 440A. The resulting output of operation 430 and/or operation 440A may be stored at the end of the initial set up process for the comparison at operation 460. Whether or not operation 440A is performed at the initial set up process, an optional operation 450 can apply the weights from the offline training of operation 440B during process 400 to the stored set up data before the comparison of operation 460. In this way, changes in the population as a whole can be used to keep the comparison up to date and new biometric features may be taken into account. The data may be stored locally in the biometric identification device 110 and accessed by server 112 by transmission or elsewise, or may be stored at server 112 for retrieval when an identifier unique to the biometric identification device 110 is transmitted (e.g., with the signals at operation 410).

Further, in some implementations, a set up process after the initial set up process may occur by which old stored data is replaced with new data. This may be done using another authentication process according to known techniques, such as through the use of a personal identification number (PIN), etc., that confirms the individual's identity before updating the feature data. This allows for use of the biometric identification device 110 even after a change in the individual's biometrics, e.g., through a change in health.

Regardless of what verification data is available for verification, the comparison of operation 460 compares that data to the output of operation 440A associated with the newly-measured biometric signals. The comparison may be done on server 112, with server 112 then sending a signal at operation 470 to biometric identification device 110 upon a match. That signal could activate the antenna of the RFID transponder of the biometric identification device 110 to transmit the identification information to a reader remote of the individual. Alternatively, the comparison may be done at the biometric identification device 110. If there is no match at the comparison of operation 460, no signal may be sent. Alternatively, a signal may be sent indicating the lack of a match that, in turn, activates an alarm or otherwise provides notice to the individual and optionally to others that there is no match. For example, a signal could be sent to a vendor at which the individual is attempting to use the device 110 that there is no match.

A match does not require all the data from the known individual to match the data from the new signals. Instead, various quantities within the data can be compared to the corresponding quantities generated from the new signals. If the differences between the pairs of quantities are all within a defined range, for example, a match may be signaled.

As used herein, information, signals, or data are received by transmission or accessing the information, signals, or data in any form, such as receiving by transmission over a network, receiving by accessing from a storage device, or receiving by user operation of an input device.

The foregoing description describes only some implementations of the described techniques. Other implementations are available. For example, the particular naming of the components, capitalization of terms, the attributes, data structures, or any other programming or structural aspect is not mandatory or significant, and the mechanisms that implement the systems and methods described herein or their features may have different names, formats, or protocols. Further, the system may be implemented via a combination of hardware and software, as described, or entirely in hardware elements. Also, the particular division of functionality between the various system components described herein is merely exemplary, and not mandatory.

The word "example" is used herein to mean serving as an example, instance, or illustration. Any aspect or design described herein as "example" is not necessarily to be construed as preferred or advantageous over other aspects or designs. Rather, use of the word "example" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such.

The implementations of the computer devices (e.g., clients and servers) described herein can be realized in hardware, software, or any combination thereof. The hardware can include, for example, computers, intellectual property (IP) cores, application-specific integrated circuits (ASICs), programmable logic arrays, optical processors, programmable logic controllers, microcode, microcontrollers, servers, microprocessors, digital signal processors or any other suitable circuit. In the claims, the term "processor" should be understood as encompassing any of the foregoing hardware, either singly or in combination. Further, portions of each of the clients and each of the servers described herein do not necessarily have to be implemented in the same manner.

Operations that are described as being performed by a single processor, computer, or device can be distributed across a number of different processors, computers or devices. Similarly, operations that are described as being performed by different processors, computers, or devices can, in some cases, be performed by a single processor, computer or device.

Although features may be described above or claimed as acting in certain combinations, one or more features of a combination can in some cases be excised from the combination, and the combination may be directed to a sub-combination or variation of a sub-combination.

The systems described herein, such as client computers and server computers, can be implemented using general purpose computers/processors modified with a computer program that, when executed, carries out any of the respective methods, algorithms and/or instructions described herein. In addition or alternatively, for example, special purpose computers/processors can be utilized which can contain specialized hardware for carrying out any of the methods, algorithms, or instructions described herein.

Some portions of above description include disclosure presented in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality. It should be noted that the process steps and instructions of implementations of this disclosure could be embodied in software, firmware or hardware, and when embodied in software, could be downloaded to reside on and be operated from different platforms used by real time network operating systems.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

At least one implementation of this disclosure relates to an apparatus for performing the operations herein. This apparatus may be specially constructed for the required purposes, or it may comprise a general-purpose computer selectively activated or reconfigured by a computer program stored on a computer readable storage medium that can be accessed by the computer.

Certain portions of the embodiments of the disclosure can take the form of a computer program product accessible from, for example, a non-transitory computer-usable or computer-readable medium. The computer program, when executed, can carry out any of the respective techniques, algorithms and/or instructions described herein. A non-transitory computer-usable or computer-readable medium can be any device that can, for example, tangibly contain, store, communicate, or transport the program for use by or in connection with any processor. The non-transitory medium can be, for example, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for tangibly containing, storing, communicating, or transporting electronic instructions.

What is claimed is:

1. A method, comprising:
   receiving, at a computing device, at least two biometric measurement signals generated by contact with a single individual, wherein the at least two biometric measurement signals comprise an electrocardiograph (ECG) signal and a photoplethysmography (PPG) signal;
   combining at least one feature extracted from each signal of the at least two biometric measurement signals to generate a combined biometric signal;
   comparing the combined biometric signal with a defined biometric signal associated with a known individual; and
   transmitting a signal, responsive to the combined biometric signal matching the defined biometric signal, indicating that the single individual is the known individual.

2. The method of claim 1, wherein combining the at least one feature extracted from each signal of the at least two biometric measurement signals to generate a combined biometric signal comprises:
   selecting at least one feature from the at least one feature extracted from each signal of the at least two biometric measurement signals as the combined biometric signal.

3. The method of claim 1, wherein combining the at least one feature extracted from each signal of the at least two biometric measurement signals to generate a combined biometric signal comprises:
   applying a weight to each feature extracted from at least one of the ECG signal and the PPG signal, wherein the weight is learned from training data collected from a plurality of individuals.

4. The method of claim 1, further comprising:
   receiving, at the computing device, at least one feature associated with the known individual and extracted during a set up process; and
   generating, using the at least one feature, the defined biometric signal using a same technique used to generate the combined biometric signal before comparing the combined biometric signal with the defined biometric signal.

5. The method of claim 4, further comprising:
   updating the defined biometric signal in response to receiving an indication that the single individual is the known individual by another authentication process.

6. The method of claim 1, wherein receiving the at least two biometric signals comprises receiving the at least two biometric measurement signals generated by a biometric identification device worn by the single individual.

7. The method of claim 6, wherein the biometric identification device and the computing device is the same device.

8. The method of claim 1, further comprising:
   storing the at least one feature from each signal of the at least two biometric measurement signals generated by contact with the known individual.

9. The method of claim 1, wherein the at least one feature extracted from each signal of the at least two biometric measurement signals comprises at least one feature determined by at least one of:
   identifying a time duration and an amplitude associated with at least one cycle of an input signal;
   performing autocorrelation and a discrete cosine transformation using a plurality of cycles of the input signal; and
   extracting at least one PQRST fragment.

10. A method, comprising:
    receiving, at a computing device, at least two biometric measurement signals generated by contact with a single individual, wherein the at least two biometric measurement signals comprise an electrocardiograph (ECG) signal and a photoplethysmography (PPG) signal;
    generating a combined biometric signal by combining the at least two biometric measurement signals;
    comparing the combined biometric signal with a defined biometric signal associated with a known individual; and
    transmitting a signal, responsive to the combined biometric signal matching the defined biometric signal, indicating that the single individual is the known individual.

11. The method of claim 10, wherein generating a combined biometric signal by combining the at least two biometric measurement signals comprises:
    generating the combined biometric signal by selecting at least one feature from features extracted from each signal of the at least two biometric measurement signals.

12. The method of claim 10, wherein generating a combined biometric signal by combining the at least two biometric measurement signals comprises:
    generating the combined biometric signal by combining a first feature extracted from the ECG signal with a second feature extracted from the PPG signal.

13. The method of claim 10, wherein generating a combined biometric signal by combining the at least two biometric measurement signals comprises:
    applying a weight to each feature extracted from at least one of the at least two biometric measurement signals, wherein the weight is learned from training data collected from a plurality of individuals.

14. The method of claim 10, further comprising:
    receiving, at the computing device, at least one feature associated with the known individual and extracted during a set up process; and
    generating, using the at least one feature, the defined biometric signal using a same technique used to generate the combined biometric signal before comparing the combined biometric signal with the defined biometric signal.

15. The method of claim 14, further comprising:
    updating the defined biometric signal in response to receiving an indication that the single individual is the known individual.

16. The method of claim 10, wherein receiving the at least two biometric signals comprises receiving the at least two biometric measurement signals generated by a biometric identification device worn by the single individual.

17. The method of claim 16, wherein the biometric identification device and the computing device is the same device.

18. The method of claim 10, further comprising:
    storing the at least one feature from each signal of the at least two biometric measurement signals generated by contact with the known individual.

19. The method of claim 10, wherein the at least one feature extracted from each signal of the at least two biometric measurement signals comprises at least one feature determined by at least one of:
  identifying a time duration and an amplitude associated with at least one cycle of an input signal;
  performing autocorrelation and a discrete cosine transformation using a plurality of cycles of the input signal; and
  extracting at least one PQRST fragment.

20. An apparatus, comprising:
  a non-transitory memory; and
  a processor configured to execute instructions stored in the non-transitory memory to:
    receive, at a computing device, at least two biometric measurement signals generated by contact with a single individual, wherein the at least two biometric measurement signals comprise an electrocardiograph (ECG) signal and a photoplethysmography (PPG) signal;
    generate a combined biometric signal by combining the at least two biometric measurement signals;
    compare the combined biometric signal with a defined biometric signal associated with a known individual; and
    transmit a signal, responsive to the combined biometric signal matching the defined biometric signal, indicating that the single individual is the known individual.

* * * * *